United States Patent [19]
van Dijk

[11] Patent Number: 5,602,289
[45] Date of Patent: Feb. 11, 1997

[54] CONVERSION OF METHANOL TO GASOLINE

[75] Inventor: Christiaan P. van Dijk, Houston, Tex.

[73] Assignee: Starchem, Inc., Houston, Tex.

[21] Appl. No.: 336,430

[22] Filed: Nov. 9, 1994

[51] Int. Cl.$^6$ .................. C07C 1/20; C07C 1/22
[52] U.S. Cl. .............. 585/315; 585/469; 585/408; 585/639
[58] Field of Search ............... 585/469, 408, 585/639, 733, 315

[56] References Cited

U.S. PATENT DOCUMENTS

| | | | |
|---|---|---|---|
| 3,391,349 | 1/1976 | Kuo | 585/408 |
| 4,035,430 | 7/1977 | Dwyer et al. | 585/408 |
| 4,404,414 | 9/1983 | Penick et al. | 585/469 |
| 4,547,602 | 10/1985 | Tabak | 585/315 |
| 4,814,536 | 3/1989 | Yurchak | 585/408 |

*Primary Examiner*—Glenn A. Caldarola
*Attorney, Agent, or Firm*—Pravel, Hewitt, Kimball & Krieger

[57] ABSTRACT

This invention relates to a process for converting alkoxy compounds into hydrocarbon compounds, mostly in the gasoline boiling range. This process proceeds with low heat exchange duty requirements for heating the alkoxy compounds and recycle streams used as feedstocks and for final cooling of reaction product gases for recovery of hydrocarbon product while at the same time offering an improved choice of operating conditions. As may be desired, steam may be added to obtain a desired final steam partial pressure in all catalyst contacts with the alkoxy compounds.

17 Claims, 2 Drawing Sheets

CONVERSION OF METHANOL TO GASOLINE

FIELD OF THE INVENTION

This invention relates to a process for converting alkoxy compounds into hydrocarbon compounds, mostly in the gasoline boiling range.

BACKGROUND OF THE INVENTION

Catalysts for the conversion of alkoxy compounds, such as methanol and/or dimethyl ether, to gasoline grade hydrocarbon products have been known since the 1970's. Processes for the conversion of natural gas and/or coal to methanol have been known for a much longer period.

Since the advent of a catalyst for the conversion of methanol to gasoline as disclosed by various Mobil Oil Corporation patents issued beginning in the 1970's, worldwide only one commercial installation which practices the methanol to gasoline ("MTG") process with a Mobil-type MTG catalyst has come into being. That installation is in New Zealand.

Conceived in the late 1970's when crude oil prices were in the $30–$40/barrel range—with projections for even further price increases—the New Zealand installation then appeared to be economically feasible. As then envisioned, and as now existing, the New Zealand facility is basically a natural gas to methanol plant (as the front end) coupled to a methanol to gasoline plant operating with an MTG catalyst in a plurality of fixed catalytic bed reactors arranged in parallel, each for single pass gas flow. The arrangement comprises five MTG reaction vessels, four of which operate at any given time and one is off stream for MTG catalyst regeneration or replacement.

Between the conception of the New Zealand facility with its attendant capital and operational cost commitments and the time that the facility was completed and ready for on-stream operations (at a capital cost obligation of about $1.2 billion) the worldwide price of crude oil drastically declined to its current day levels of about $20/barrel. At today's cost of crude oil, gasoline produced from methanol by a process as followed in the New Zealand facility is competitively uneconomical in comparison to gasoline refined from crude oil. In the first place the New Zealand approach is too costly in the conversion of natural gas into methanol. The present inventor, together with Lowell D. Fraley, has described a natural gas to methanol conversion process with much lower expected capital costs in U.S. Pat. Nos. 5,177,114 and 5,245,110. Yet, even with this expected lower cost for methanol the New Zealand process of converting methanol to gasoline is still too high in capital cost.

A major reason that the methanol to gasoline part of the New Zealand facility is uneconomical is because of the heat exchange duties—both in capital and operational cost—required for proper operation of a Mobil-type methanol to gasoline catalyst (MTG catalyst). For proper operation of an MTG catalyst in terms of its activity and aging, it must be exposed to a particularly controlled environment of temperature and water concentration while it is in contact with the methanol (or other oxygenated compounds) that it converts to gasoline grade hydrocarbons. If exposed to too low of a temperature, an MTG catalyst will not be active or will be of such low catalytic activity to be of no interest. Exposed to too high of a temperature, the MTG catalyst will so prematurely "age" and/or be destroyed so as to be economically impractical for use.

This problem of the temperature sensitivity of an MTG catalyst is compounded by the problem of its need for the presence of water in order for it to be catalytically active. Too little water in its presence and it is inactive or of such low activity to be of little practical interest. Depending upon its temperature exposure, too high a concentration of water and the MTG catalyst ages so prematurely and/or is destroyed so as to render its economical use unfeasible.

These temperature/water sensitivity problems attendant to use a MTG catalyst are further complicated by the fact that the reaction of methanol (or other oxygenated compounds) to gasoline which it catalyzes is fast and highly exothermic, thus causing a high degree of heat release (i.e., heat of reaction) at the site of the desired reaction. If not moderated by some means, a methanol and/or dimethyl ether feedstock fed into contact with an MTG catalyst at 710° F. would react in contact with the catalyst to form a product gas having a temperature greater than 2,000° F. Such a temperature rise within an MTG reaction vessel is not acceptable. Nor can the heat released by the MTG reaction be controlled within acceptable product gas exit temperature limits—i.e., 730° F. to 800° F.—by direct heat exchange methods, because the reaction MTG is too fast.

The need of an MTG catalyst for a sufficient, though limited, exposure to water coupled with its need for exposure to a sufficient, though limited, range of temperature to be sufficiently active, coupled to the fact that it catalyzes a fast and highly exothermic reaction, have entailed a number of processing complexities associated to the heat exchange requirements attendant to the proper operation of a methanol to gasoline process with an MTG catalyst.

In order to accommodate the temperature range exposure requirements of the MTG catalyst, the New Zealand facility effectuates product gas temperature control within the MTG catalyst vessels by recycle of the $C_2$ and $C_{3+}$ hydrocarbon by-product gases remaining after the reactor product gases are cooled down from their reaction temperature of about 800° F. to about 100° F. for removal of their gasoline grade hydrocarbon product content. In order to limit the temperature rise in the MTG reaction to less than about 100° F., this recycle diluent gas is added in an amount compared to the methoxy feed gas (methanol, dimethyl ether, etc.) of about 12.4 moles diluent recycle/mole methoxy equivalent. For every 1 volume of methoxy equivalent with which it is combined to form the feedstock gas it is therefor necessary to heat about 12.4 volumes of the $C_2$ and/or $C_{3+}$ recycled diluent gas from its recovery temperature of about 100° F. to the minimum temperature required by an MTG catalyst for sufficient activity, which is about 650° F. and preferably about 700° F. This imposes a tremendous heat exchange burden both in terms of reactor effluent gas cool down (800° F. to 100° F.) for gasoline product recovery and recycle gas ($C_2$/$C_{3+}$) reheat (from 100° F. to at least 650° F., and preferably to 700° F.). For each volume of hydrocarbon product produced and recovered about 71 volumes of recycle diluent gas must be heated up by about 600° F. and later cooled down by about 700° F. in adiabatic heat exchanger units by heat exchange first with a new portion of cool feed gas and then by cooling water or a refrigerant.

In the New Zealand operation the methoxy compound, generally in the form of an equilibrium mixture of methanol, dimethyl ether and water vapor, is combined with a recycle gas comprising $C_2$ and $C_{3+}$ hydrocarbons and the methoxy content is reacted in a single pass over an MTG catalyst to produce a product gas of about 800° F. with a partial pressure of water (as steam) of 0 about 2 atmospheres absolute (ata) at a product gas pressure of about 22.3 ata.

Hence, heat exchange operations to heat up feed gases and/or cool down product gas are carried out on gas streams at a pressure of about 22.3 ata.

The MTG reaction gases are cooled from their reaction temperature, $T_R$, to their final cooldown temperature, $T_O$, in two heat exchange operations. In the first operation the reaction gases are indirectly heat exchanged with feed gases through adiabatic heat exchangers to cause the feed gases to warm up from their unit available temperature of about $T_O$ to their reactor inlet temperature $T_I$ by transferring thereto of a quantity of heat Q from the reaction gases which thus causes the reaction gases to cool down from their reaction temperature $T_R$ to their first cooldown temperature $T_x$. Thereafter, the reaction gases are finally cooled from their first cooldown temperature $T_x$ to the liquid hydrocarbon recovery temperature, $T_O$, either by direct or indirect heat exchange contact with chill water.

For purposes of discussing the heat exchange burden associated to operation of the New Zealand process, one may assume that the specific heat content of a feed gas about equals the specific heat content of the reaction product gas which results therefrom. Under this circumstance, when the reaction product gas gives up a quantity of heat Q to heat up a new portion of feed gas from $T_O$ to $T_I$ the reaction gas cools to a temperature $T_x=T_R-(T_I-T_O)$. To finally cool the reaction gas to a temperature $T_O$ to recover its liquid hydrocarbon content the quantity of heat that must be removed from the reaction product gas is that additional quantity of heat resulting from the heat of reaction of the alkoxy compound from which the reaction gas was formed.

Generally, the adiabatic heat exchangers through which feed gas is heated up while reaction product gas is cooled down are on the order of 3–4 times as expensive as those heat exchange units by which the product gas is finally cooled down by heat exchange with chill water. Further, the sizing of each of these heat exchange units, which bears very significantly on their cost, is directly effected by the difference in temperature to which the feed gases are to be heated and the temperature from which the product gas is to be cooled ($\Delta T$) and the pressure (P) of the gases to be heated and cooled. The larger the differential temperature ($\Delta T$) and/or the higher the pressure the more efficient the heat exchange process and the smaller can be the size of the heat exchanger needed. The relative heat exchange surface area ($A_R$) required to transfer this quantity of heat (Q) is generally given by the formula $A_R=Q (1/\Delta T)(1/P)^{0.6}$.

Suggestions have appeared in the prior art which are directed to ameliorating this tremendous heat exchange burden. Mobil Oil Corporation's U.S. Pat. No. 4,035,430 to Dwyer et al. describes an MTG process wherein a number of spaced apart MTG catalyst beds are employed and hydrocarbon recycle gas may be injected between the successive beds to control the exotherm. Also described is the possibility of interbed injection of methanol or DME as a quench to maintain the temperature rise in each MTG catalyst bed to about 50° F. with a total temperature rise over all beds to about 200° F. This however, as Mobil's later U.S. Pat. No. 4,404,414 to Penick et al. notes, requires either that the conversion of the alkoxy feed in each MTG reactor be limited to a relatively low value (which is difficult to control at the high reaction rate in contact with the catalyst) or, alternatively, that an extraordinarily high recycle ratio must be used, neither being an attractive possibility.

Mobil's U.S. Pat. No. 4,404,414 to Penick et al. provides yet another suggestion. It describes the use of the reactor effluent gas of a preceding MTG reactor, for admixture with a fresh charge of alkoxy compound (DME and/or methanol) to be fed to a succeeding MTG reactor, as the medium for heating up the new alkoxy charge of combined gas mixture to the inlet temperature desired for reaction in a succeeding MTG reactor. According to Penick et al.'s suggestion the total quantity of temperature-control diluent gases used in the process is passed through the first MTG reactor and hence into the succeeding MTG reactor without the need for cooldown heat exchange of the diluent gas from the reaction gas temperature (about 800° F.) to about 100° F. for purposes of product recovery and thereafter reheat from about 100° F. to an inlet reaction temperature (about 700° F.) for recycle use with the new alkoxy charge. This reduces the overall effective volume of recycle gas as a ratio to the final product make required for proper temperature moderation in the MTG reactors. However, this heat exchange savings is purchased at the risk of advanced aging of the MTG catalyst in the succeeding MTG reactor that may result from the successive accumulation of water (steam) content that results from the buildup of water as a by-product of the MTG reaction that occurs within both the preceding and succeeding reactors. For example, for each mole of hydrocarbon produced, the hydrocarbon product from crude methanol having a water content of about 6 wt. % or from an equilibrium methanol-dimethyl ether mixture produced therefrom contains about 6.45 moles of water. Addition of a diluent gas to this methoxy compound in an amount sufficient to moderate the temperature rise in a first MTG reactor as desired, followed by addition to the first reactor product gas of an equivalent amount of new methoxy compound to form a feed gas stream for reaction in a second MTG reactor results in a product gas from the second reactor having nearly double a mole fraction of water as that of the product gas from the first MTG reactor.

Accordingly, in the process proposed by Penick et al. where both reactors are operated at about the same pressure the concentration of water (as steam) to which the MTG catalyst of the succeeding MTG reactors is subjected is substantially greater than that to which the MTG catalyst of the preceding MTG reactor is exposed. This, as Penick et al. notes, inevitably leads to the dilemma that if both reactors are operated at about the same temperature either the MTG catalyst in a preceding MTG reactor must be under-utilized by depriving it of exposure to a water content that optimizes its potential for activity or the MTG catalyst in a succeeding MTG reactor must be overexposed to water such that it ages prematurely. This dilemma of Penick et al.'s proposal necessitates a significant difference in the operational conditions of temperature or pressure between the preceding and succeeding MTG reactors, which, in order to maximize both the activity and operational life of the MTG catalyst in each, results in an undesirable change in hydrocarbon product's compositional distribution produced in each.

Yet another Mobil Oil Corporation U.S. Pat. No. 4,788,369 to Marsh et al. suggests a method for improving the economies of even the Penick et al. process that involves the separation of the $C_{3+}$ by-product hydrocarbon gases from the $C_{2-}$ by-product hydrocarbon gases and thereafter use of the $C_{3+}$ hydrocarbon gases as the recycle diluent gas required for temperature moderation. Because of the higher specific heat of the $C_{3+}$ recycle, following the suggestion of Marsh et al. the volume of recycle diluent gas required for practice of the MTG process may be reduced. As Marsh et al. notes, in terms of compressor duties a $C_{3+}$ recycle gas is more readily and economically processable for recycle use than is a $C_{2-}$ recycle gas. However, a smaller amount of the $C_{3+}$ recycle gas volume necessitates use of a lower total pressure for processing if the steam vapor pressure is to be kept the same as before. That lower pressure has a negative effect on the heat exchange capability of the process. Thus, the only advantage remaining for the Marsh approach is the use of fewer moles of recycle gas which thus reduces compressor duties. The disadvantages of increased heat exchange surface requirements resulting from the lower pressure of operation reduces, and might even outweigh, the savings in the recycle compressor. It suffices to say that the Marsh et al. patent does not succeed in diminishing the heat exchange requirements of the process. Yet, even with use of a $C_{3+}$ hydrocarbon by-product gas as a recycle to save on compressor duties as suggested by Marsh et al. the savings in capital and operational cost of the Marsh et al. process requirements are modest, at best.

The temperature rise/water concentration dilemma that hamstrings the MTG conversion process over an MTG catalyst as being an economically competitive process for gasoline production compared to that of gasoline refined from natural crude oil remains unsolved by any prior art suggestion. Given the abundance of natural gas reserves from which the production of gasoline grade products is technologically possible, a solution to the economical obstacle to its conversion to gasoline is a greatly desired goal.

SUMMARY OF THE INVENTION

In accordance with the process described by this invention, it is possible to substantially reduce the heat exchange duties entailed in the proper operation for activity and aging regulation of an MTG catalyst while also properly controlling the exposure of such catalyst to a water concentration.

To significantly reduce the heat exchange requirements for proper temperature control of the reaction of an alkoxy compound over an MTG catalyst, and at the same time control the steam partial pressure in the process within narrow limits, aiming thus to have the reaction proceed under proper temperature and steam pressure control without at any time endangering the MTG catalyst, the invention proposes a method for operation of an MTG process wherein:

(1) Successive reaction zones containing an MTG catalyst are employed wherein a product effluent gas of temperature $Tr_P$ from a preceding MTG reaction ($r_P$) is combined with a new charge of feed gas comprising an alkoxy compound and a diluent gas comprising a $C_{2-}$ recycle gas, a $C_{3+}$ recycle gas, steam, hydrogen, or mixtures thereof, which new charge of feed gas has been preheated to a temperature $T_P$ that is less that $Tr_P$, and the mixture of the new charge of feed gas with the product effluent gas forms a combined gas mixture that is of a desired temperature $T_I$ and specific heat content to be contacted with an MTG catalyst in a succeeding reaction zone ($r_s$) to convert its alkoxy compound content to hydrocarbon products contained in a new product gas stream having a temperature $Tr_S$. In warming up the new alkoxy-recycle feed gas charge from the preheat temperature $T_P$ by mixing with the earlier hot effluent gas to obtain a combined gas mixture of temperature $T_I$ the warmup is obtained without heat exchangers, which otherwise would have been necessary to warm the new feed gas up to the desired reactor inlet temperature; further the lower diluent recycle content of the fresh feed gas would not allow entry of that feed as such at the desired reactor inlet temperature without its reaction to a temperature greater than the $Tr_S$ temperature desired for the outlet from the reactor.

(2) The new charge of alkoxy compound provides an alkoxy equivalent value which exceeds that which was added to the preceding MTG reaction zone and the new charge of diluent gas provides the combined gas stream with a specific heat content that upon reaction of the new charge of alkoxy compound to hydrocarbon compounds limits the temperature rise ($\Delta T_R$) within the succeeding reaction zone to less than 100° F. and preferably less than 75° F.

(3) The new charge of alkoxy compound and diluent gas are preheated before combination with the product effluent gas to a temperature $T_P$ that is below the desired reactor inlet temperature $T_I$, so that on taking an appropriate amount of this new charge for addition to the effluent gas from the preceding reactor a mix temperature of $T_I$ will be obtained, whereafter contacting the combined gas mixture with a sufficient amount of MTG catalyst the succeeding reaction will produce a new effluent gas temperature of $T_R$, which is at a desired level. As desired, each MTG reactor in the series may be operated with the same $T_I$ and $T_R$ temperatures or any reactor within the series may be operated at a $T_I$ and $T_R$ temperature selected for it which is different than that of other reactors in the series, this being accomplished by the proper choice of the alkoxy and recycle content of the new feed gas charge to be added to the succeeding reactor and the quantity of this new feed charge to be combined with the product effluent gas from the preceding reaction.

(4) As desired, a portion of the new charge of diluent gas may comprise water in an amount that together with the water carried over with the product effluent gas and the water formed by reaction of the new charge of alkoxy compound provides a total water content in the new product effluent gas that at the outlet pressure of the succeeding MTG reaction zone provides for any partial pressure of water desired, which preferably will not exceed 2.2 ata, and preferably will be in the zone of 1.85 to 2.2 ata, most preferably in the zone between 1.95 and 2.15 ata.

In its general form the process of this invention may seem complicated with respect to how the process conditions can be set and kept at necessary conditions in order to achieve the desired goal. Therefore the invention will first be explained in its simplest form. Assume that it is desired to have a series of reactors, in all of which the reaction of the methoxy compounds is taking place in the same reaction temperature zone ($T_I$ to $T_R$) and also where all the reaction product gases have identical steam vapor pressures.

This target can be achieved even though substantial pressure drops exist between reactor zones. Again, it is easier to explain the invention if the simplifying assumption is made that the pressure drop between reactors is so small that it can be ignored.

It is clear that given a chosen composition of the diluent recycle, conversion of a given amount of a given methoxy compound can be kept in a single reactor in a desired reaction temperature zone, say from 700° to 800° F., by proper choice of the quantity of the diluent recycle gas added to the methoxy compound. Choose now, however, a smaller quantity recycle gas, which would then necessitate a larger reaction temperature zone, but with the same final temperature, say between 600° and 800° F. Also choose a pressure at which to operate so that on reaction the resulting water vapor partial pressure is at the desired level.

Now take a large quantity of such an alkoxy-recycle gas mixture and preheat that to the temperature of 600° F., but do not as yet contact the so preheated gas with the MTG catalyst. Take a starter gas stream at the desired final temperature level of 800° F. with the desired level of water vapor partial pressure at the desired total pressure. Such a starter gas stream could be of any composition, but could conveniently be made from the same alkoxy compound in admixture with a similar diluent recycle composition, but in a larger recycle amount, so that that the starter stream could be warmed up to 700° F. and contacted with MTG catalyst to react to a product gas having a temperature of 800° F.

Now take of the new mixture of alkoxy and recycle that has been preheated to 600° F., and in a sufficient amount mix it with the hot starter gas stream which is at 800° F. to arrive at a combined gas stream having a temperature of 700° F. On reaction of the alkoxy content of the combined gas stream over an MTG catalyst the final temperature of the product gas will then be 800° F., because each component part of the combined gas stream was once at or could react to this temperature.

The product gas stream at 800° F., thus obtained, serves in its own turn as a hot gas source for admixture with a new portion of the 600° F. gas mixture containing new alkoxy compound to arrive at a still larger volume 700° F. combined gas stream which again can be contacted with an MTG catalyst to form a product gas stream at 800° F. This alternating mixing and reaction is continued until all the alkoxy containing gas mixture of 600° F. has been reacted.

When pressure drop across the MTG reactor(s) is sufficiently large to have to be taken into account; then on each addition of the 600° F. alkoxy-containing gas a sufficient amount of steam may be added also, so as to arrive at the desired water partial pressure at the resulting lower total pressure due to pressure drop. A reduction is then needed of the amount of the diluent recycle gas content of the new charge by an amount that corresponds to the specific heat content of the added steam, so that the (slightly) changed 600° F. stream still will be able to react to 800° F. Alternatively, with no alteration of the alkoxy-containing gas mixture, the same results can be obtained by adding the requisite amount of 800° F. steam to the product effluent gas or to the 600° F. alkoxy-containing gas.

The given procedure can obviously also be applied to a narrower reaction temperature zone than 700° to 800° F. and to different starting temperatures for the gas mixture subjected to reaction than the value of 600° F. chosen for this discussion.

It is also clear that it is possible to vary the steam partial pressure from reactor to reactor, if desired. Such steam partial pressure variations are easier in an upward direction than downward.

A further advantage is that the temperature zone of reaction can be varied at will from reactor to reactor by changing the amount added of the new alkoxy-recycle charge and its preheat temperature.

It should therefore be clear, that this invention provides a feasible method to have the MTG reaction proceed within desired limits of temperature and also attain the desired water vapor partial pressure levels in the exit of each of the reactors.

It is the primary intent of this invention to lower the cost of the heat exchange which is a major cost item in the New Zealand design. However, it should also be pointed out that the present invention opens the possibility for operating a series of reactors under an innovative temperature and steam partial pressure approach.

It has been discussed in the literature that at low temperature a large percentage of aromatic hydrocarbons are formed in the MTG reaction. When the MTG reaction then proceeds to higher temperatures, the aromatics previously formed are alkylated with the methanol which is still being reacted at these higher temperatures. When it is desired to lower the content of higher alkylated aromatics, like durene and even the trimethylated benzenes (as presently desired for achieving a high quality reformulated gasoline), with this invention it then becomes feasible to operate the first set of MTG reactors at a higher inlet temperature, thus lowering the formation of aromatics to a very low amount and only in the last MTG reactor allowing operation at a lower temperature, but finishing the reaction in that lower temperature zone. This thus translates to an operation of the first four of, say five, reactors at a temperature zone of for instance 720° to 790° F., while the last MTG reactor can be kept within the narrow temperature limits of for instance 700° to 740° F. The larger amount of aromatics formed in the last reactor can then not be further alkylated above the 740° F. temperature.

According to this invention the total amount of alkoxy equivalent processed to hydrocarbon products is proportioned among a plurality of MTG reaction zones and the alkoxy equivalent quantity provided to each MTG reaction zone generally increases in progression from the first to the last or final MTG reaction zone. This method of operation provides for great flexibility in the operational conditions of temperature and pressure at which a given MTG reaction zone may be operated relative to another in order to achieve a variety of desirable objectives, all attendant with a significant reduction in the heat exchange duties otherwise required to process the same total amount of methoxy equivalent to hydrocarbon products by prior MTG processing methods.

For instance, where the activity of the MTG catalyst is the same in each zone, for uniformity of product distribution of hydrocarbon product produced in each MTG reaction zone, each desirably is operated at approximately the same pressure, the same inlet and outlet temperatures (i.e., each zone has the same $\Delta T_R$), and each reaction zone, at least after the first, has about the same partial pressure $H_2O$ at the outlet of the reaction zone. Such is possible with the method of the invention. However, if because of aging or other reasons the activity of an MTG catalyst in one of the multiple zones is significantly less than another, it may be desired to operate this particular MTG reaction zone at a higher outlet partial pressure of $H_2O$ than the other, or at a higher $T_R$, this in order to enhance Lhe activity of the MTG catalyst therein. This too is ossible with this invention.

A combination of factors leads to a significant reduction in the heat exchange duties required by the process of this invention in comparison to prior MTG processes employed or proposed. First, on the bases of the total methoxy equivalent ("MeO eq.") processed, with the process of this invention the diluent gas/MeO eq. mole ratio is reduced which in turn reduces the quantity of diluent gas that through adiabatic heat exchange units must be preheated for reaction temperature moderation use or, ultimately, cooled down for recovery of hydrocarbon product. This reduces the size of the heat exchangers required for feedstream heatup and/or final product cooldown. Further, a significant quantity of the total methoxy equivalent processed, together with the recycle diluent gas needed to moderate its heat of reaction, needs to be preheated to a temperature ($T_P$) which is lower than the temperature ($T_I$) at which it is desired to contact the methoxy compound with an MTG catalyst. This is achieved by admixing the methoxy-recycle feed with hot product gases from a preceding MTG reaction (at $T_R$) which heats up the added methoxy-recycle feed to the desired reaction inlet temperature, while cooling down the hot reaction gases to the desired reaction inlet temperatures. In this respect this aspect of the feed gas heatup/product gas cool down is performed by direct gas-gas contact, thus eliminating this portion of need for adiabatic heat exchange equipment. Also, with respect to the warmup of feedstock gases to $T_P$ by heat exchange with reaction gases at $T_R$ through an adiabatic heat exchanger, this also increases the heat exchanger differential temperature ($\Delta T$) making the heat exchange process more efficient, meaning the heat exchanger need will be smaller.

As explained hereafter in greater detail, operations in accordance with this invention permit a selection of conditions in terms of (a) the nature of the methoxy feed, (b) the nature of the diluent gas composition, and (c) the temperature to which the feed gases are preheated before being mixed with reaction gases from a preceding MTG reaction; such that the MTG conversion can be achieved with the maximum of economy in terms of the capital and/or operational cost associated therewith.

DESCRIPTION OF THE PREFERRED EMBODIMENTS

Figure 1:
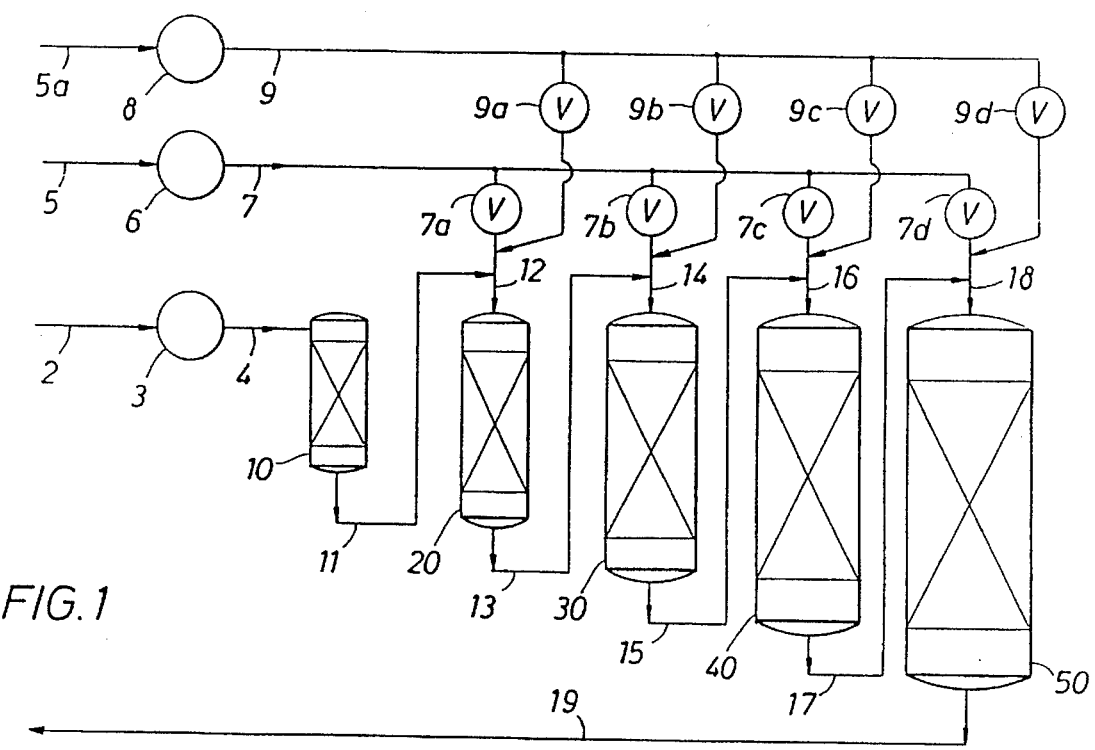
FIG. 1 is a schematic illustration of a five reactor series with interstage feed of feed charges of alkoxy-recycle feedstock gases between the reactors in accordance with the present invention.

The practice of this invention requires an alkoxy feedstock, generally a MeOH and/or DME feedstock, various reaction vessels containing an MTG catalyst composition and devices for controlling the rate of feed of DME and/or MeOH and $H_2O$ (as steam), $C_{2-}$ and $C_{3+}$ gas by-product as diluent recycle gaseous feedstock admixture components of the total feedstocks to an MTG catalyst containing reaction vessel.

The MeOH may be formed from a coal or natural gas starting material by any of the methods well known to those skilled in art. Preferably when produced from natural gas the methanol is produced by methods as described in U.S. Pat. Nos. 5,117,144 and 5,245,110. Prior to the MTG reaction, and preferably so, the MeOH may be subject to contact with a dehydration catalyst as is well known in the art to convert it to an equilibrium mixture of MeOH, DME and $H_2O$ and this gaseous mixture of oxygenated organic components which is a preferred alkoxy feed component for an MTG catalyst contact for conversion to a hydrocarbon product with production of by-product water. Most preferred is the use of DME alone as the alkoxy feed component. DME can easily be isolated from the equilibrium mixture and the remaining methanol-water can be concentrated as to its methanol content and recycled back to contact with the dehydration catalyst to make more DME containing equilibrium mixture.

The MeOH and/or DME components, however made, are, in the process of this invention, brought into contact with an MTG catalyst composition, as described in U.S. Pat. Nos. 4,404,414; 4,788,369 to Penick and Marsh as earlier discussed and in other Mobil U.S. patents, to catalyze their conversion into a hydrocarbon product, a significant portion of which is within the gasoline boiling point range. As a rule of thumb, the carbon atoms supplied by the methoxy content of the DME/MeOH feed gas composition are converted to a hydrocarbon product averaging a carbon atom content of about 5.8—i.e., $C_{5.8}H_{13.6}$. This hydrocarbon product is, of course, comprised of a mixture of hydrocarbons which vary in carbon atom numbers from one up. The $C_{1-5}$ carbon atoms products of this reaction are normally gaseous compounds and are recovered and at least a portion thereof is recycled as a diluent gas to become a part of a fresh alkoxy feedstock to an MTG reactor, together with traces of higher hydrocarbons. Most of the $C_{5+}$ carbon atom hydrocarbon products are recovered as a "gasoline" or fuel grade product. The $C_{2-}/C_{3+}$ hydrocarbon gas by-products of the MTG reaction which are recovered may be separated into separate $C_{2-}$ and $C_{3+}$ steams, and either alone or in desired combinations thereof recycled to the MTG process for purposes of temperature control.

In order to minimize the heat exchange duty requirements while regulating the temperature, pressure and water concentration conditions for the proper activity and aging regulation of an MTG catalyst during the conversion of alkoxy compounds to hydrocarbon products, the process of this invention utilizes a plurality of MTG catalyst zones or reaction vessels in series flow whereby the product effluent gas from any preceding MTG zone or reactor is combined with a fresh charge of alkoxy compound together with a recycle diluent gas and/or water (stream) to form a combined gas steam of a temperature and specific heat content suitable as an alkoxy-containing feed gas to a succeeding MTG zone or reactor wherein its alkoxy compound content is reacted in contact with an MTG catalyst to hydrocarbon compounds. Generally, the alkoxy equivalent of the alkoxy compound added to the product effluent gas of a preceding MTG reaction exceeds the alkoxy equivalent content of the feed gas stream to the preceding reactor from which the product effluent gas was produced.

Any number of MTG reaction zones or reactors may be utilized, though generally no further practical advantage is realized in excess of ten, and more preferably five to eight MTG reaction zones or reactors in series. The product effluent gas from the final MTG reaction of the series is cooled from its final reaction temperature to about 100° F. to recover its liquid hydrocarbon content separate from its $C_{2-}$ and $C_{3+}$ gaseous hydrocarbon content. At least a portion of $C_{2-}$ and/or $C_{3+}$ gaseous hydrocarbon by-product is recycled for use as a temperature moderating diluent gas for combination with fresh charges of alkoxy compound and the recovered liquid hydrocarbon is further refined into its various boiling point fractions for use as fuels or other purposes.

The combination of a fresh charge of alkoxy compound and $C_{2-}$ and/or $C_{3+}$ recycle gas with the product effluent gas from a preceding MTG reaction to form a combined gas of suitable inlet temperature ($T_I$) and specific heat content as feed to a succeeding MTG reaction reduces the overall heat exchange duties with respect to the total make of hydrocarbon product by reducing the size of the heat exchangers needed for heating the fresh charge to the temperature to which the fresh charge of alkoxy compound and recycle gas must be preheated to condition it for admission to the succeeding MTG reactor, which mixture in line with its alkoxy content and its total specific heat content will react in contact with an MTG catalyst from a temperature of $T_I$ to the desired temperature $T_R$ for the new reactor.

For example, conversion of 100 MPH of methanol (MeOH) creates a heat of reaction ($Q_R$) of 100×24,000 BTU/lb-mole MeOH=2,400,000 BTU. To limit the temperature rise of the reaction gases to $\Delta T_R$=75° F. for a gas inlet temperature $T_I$=710° F. and an effluent gas outlet temperature $T_R$=785° F. the total specific heat content of the feed gas must be 2,400,000/75=32,000 BTU/° F. Hence recycle diluent gas is combined with this methanol in an amount to provide a total feed gas of this specific heat content. To preheat this total feed gas from its unit available temperature $T_O$ of, say, 100° F. to the reactor inlet temperature $T_I$ of 710° F. requires the addition of heat to such gas that is (710–100)×(32,000)=19,500,000 BTU On the other hand were a quantity of recycle diluent gas added to this methanol that would allow it to increase in temperature by 150° F. due to the reaction of methanol, the total feed gas would have a total specific heat content of 2,400,000/150=16,000 BTU/° F., meaning there would be less recycle diluent gas added. This feed gas could then react from a temperature of 635° F. to a product gas of 785° F. Then to preheat this total feed gas stream from 100° F. to 635° F. would require the addition of heat of (635–100)× (16,000)=8,560,000 BTU. By mixing this 635° F. temperature gas having a specific heat content of 16,000 BTU/° F. with a gas stream having a temperature of 785° F. and a specific heat content of 16,000 BTU/° F. a combined gas stream is formed having a temperature of 710° F. and a total specific heat content of 32,000 BTU/° F. Thereafter, reaction of the methanol content of this combined gas stream will increase the temperature of the gas by 2,400,000/32,000= 75° F. to provide an effluent gas stream having an outlet temperature $T_R$ of 785° F.

As seen from the above, the quantity of heat exchange required for warmup of the feed gas is significantly reduced because the quantity of recycle diluent gas is reduced, but the methanol is still converted in the same temperature zone, i.e., 710°–785° F. Further, the efficiency with which the feed gas warm-up heat exchange is accomplished is significantly enhanced by reason of the increase in the differential temperature ($\Delta T$) at which the heat exchangers performing this duty operate. On one hand, the 710° F. warm-up situation would require a heat exchanger surface area ($A_R$) of $A_{R710}$= 19,500,000 $(1/P_{710})^{0.6}$ and the 635° F. warm-up situation would require $A_{R635}$=8,560,000$(1/P_{635})^{0.6}$. The savings in heat exchange duties to be realized through the change in the differential temperature of heat exchange operations would only be offset if the difference in the pressure (P) of the two operations were such that for the 635° F. warm-up situation the pressure for operation was less than one-twelfth (1/12) that for operation of the 710° F. warm-up situation. However, the change in the recycle GAS amounts between the two situations does not require such drastic reduction in the pressure of operation in order to maintain the same partial pressure of steam in the two product gases.

In these embodiments of the process of this invention wherein the first MTG reactor of the series operates on a feed gas composition that is preheated through adiabatic heat exchangers to the $T_I$ temperature desired for its contact with the MTG catalyst therein, the heat exchange duty that this reactor contributes to the total heat exchange duty of the overall process is significantly greater in comparison to the quantity of methoxy equivalent converted therein than is that contributed to the total by the subsequent MTG reactors of the series. Hence, by using a larger number of reactor steps, the influence on the total heat exchange duties of the warmup for the first reactor is greatly reduced so that the benefit for the reduction in heat exchange for the subsequently added feed gas material is then almost totally available as the gain for this reaction choice. The number of reactors utilized together with the conditions chosen for their operation is preferably such that no more than 20% of all alkoxy compound converted by the process is converted in the first reactor of the series, preferably no more than 10%. As made clear in the examples, the reduction of the total heat exchange duties in comparison to that for a single reaction stage processing of the same quantity of methoxy equivalent is substantial and can be as much as a reduction by about an order of magnitude of.

The heat exchange is further facilitated by using an alkoxy feed which will make a lower steam fraction and can therefore be used at higher pressure, which facilitates the heat exchange. Such feeds may be obtained by removing water from the alkoxy feed. Removing water from methanol is possible by distillation but that is a rather difficult operation. It is easier to remove steam from dimethyl ether, which can easily be made from methanol by contact at high temperature over an acid catalyst like alumina. The then unconverted methanol and most of the water present can easily be separated from the DME and recycled back to the DME conversion reactor. Use of the DME as the alkoxy feed for hydrocarbon production reduces the amount of water generated in the MTG reaction to only 0.5 mole water per mole of alkoxy equivalent, as against 1.3 for a methanol stream containing 30% of this methanol molar content as water.

Another means for increasing the efficiency of the heat exchange operations required is to employ a diluent gas composition containing low molecular weight species, like hydrogen, and/or species of a low specific heat value. Hydrogen for addition to the $C_{2-}$ and/or $C_{3+}$ diluent recycle gas can be provided out the methanol production unit by diffusion of the tail gas therefrom through a membrane preferential for permeation of $H_2$ relative to other gas species. Further, use as a diluent gas of a recycle which is rich in the $C_{2-}$ hydrocarbon by-product allows operations at a higher total pressure while providing for the same partial pressure of steam in the product gas than does a diluent gas rich in the $C_{3+}$ hydrocarbon by-production. The higher operational pressure provided by use of a $C_{2-}$ rich recycle provides for more efficient heat exchange of the feed and product gases by a factor of $(1/P)^{0.6}$.

With the process of this invention the operation of each MTG reactor in the series at the same inlet and outlet temperatures and at about the same partial pressure of steam at the outlet without significant changes of pressure therebetween becomes possible (i.e., allowing only for the pressure drop across each reactor needed for gas flow)—thus providing for uniformity of product distribution production in each of the reactors. For example, with reference to use of dry methanol as the fresh alkoxy feed for each MTG stage, wherein the quantity of methanol feed doubles with each succeeding stage, when dry methanol is used as the first stage feed the partial pressure of water in the product gases of the early MTG stages is significantly lower than that of the later MTG stages. Hence, wherein the last MTG stage is operated at an outlet pressure that provides for a partial pressure of water of 2 ata, the first MTG stage operates at an outlet pressure that provides a partial pressure of water of about 1,015 ata. However, by adding water (steam) to the dry methanol feed to the first stage, and/or as needed or desired in the fresh methanol feed to later MTG stages, it is possible to operate each MTG reactor at substantially the same partial pressure of water at its outlet without significantly reducing the pressure at which the last MTG reactor operates. It is also possible, as desired, to operate a succeeding reactor at a condition of an inlet-outlet temperature or a pressure that significantly differs from the operating conditions of preceding reactors without exceeding a partial pressure of steam therein that would prematurely age or destroy its MTG catalyst content—to permit the control of final product distribution, such as to minimize the durene content of the hydrocarbon product.

Nature of the Alkoxy Feed

Whatever the precise nature of the alkoxy feed, typically it will be available for use at about 100° F. following its production and cooling to condense excess water from it. Although an MTG catalyst is active for production of hydrocarbon products with respect to any alkoxy compound—i.e., alkanols, alkylethers, and combinations thereof—and the process of this invention is applicable to the use of any suitable alkoxy compound; conventionally the alkoxy compound used is methanol, dimethylether, or equilibrium mixtures thereof produced by the catalytic dehydration of methanol. Hereafter, the process of this invention is described with respect to methoxy compounds—i.e., methanol (MeOH), dimethylether (DME), and mixtures thereof (MeOH+DME). Further, reference to the amount of hydrocarbon products of which the methoxy compound is capable of production is referred to by its "methoxy equivalent." For example, for a hydrocarbon product having an average carbon number value of 5.8 carbon atoms, the following equations apply:

(1) $5.8 \text{ MeOH} \rightarrow (C_{5.8}H_{13.6}) + 5.8 \text{ H}_2\text{O}$ (2) $5.8 \text{ DME} \rightarrow 2(C_{5.8}H_{13.6}) + 5.8 \text{ H}_2\text{O}$ Hence, each mole of MeOH presents one methoxy equivalent and each mole of DME presents two methoxy equivalents.

Within the context of this invention the methoxy compound employed as feed may be methanol only, dimethyl ether only, or mixtures thereof together with such water vapor content as is normal to their production or, preferably, after water that is condensable at about 100° F. has been separated therefrom. The nature of the methoxy composition selected as fresh feed to an MTG reactor affects the nature and/or quantity of diluent gas with which it must be combined for proper moderation of the temperature rise and water concentration control within an MTG reactor. On a methoxy equivalent basis, each mole of MeOH releases a greater quantity of heat (24,000 BTU/lb-mole) and H$_2$O by-product (1 mole H$_2$O/mole) than does DME (½ mole H$_2$O/mole and 35,200 BTU/lb-mole). Further, since the specific heat of MeOH (16.94 BTU/° F./lb-mole) and DME (25.08 BTU/° F./lb-mole) differ, the composition of the methoxy feed selected influences the degree to which the methoxy+recycle diluent gas composition must be preheated before its admixture with the product effluent gas from a preceding MTG reactor to yield a combined gas stream of suitable temperature and specific heat content for feeding to a succeeding MTG reactor.

An ideal case for purposes of achieving the greatest economics in the overall heat exchange requirements for the hydrocarbon production process is that of exclusive use of DME as the methoxy compound. Next in order of preference is that of the use of a dehydration equilibrium mixture of MeOH+DME as the methoxy feed.

The MTG Catalyst

A variety of compositions have been disclosed as suitable catalysts for the conversion of methoxy compounds to hydrocarbon compounds, as for instance in U.S. Pat. Nos. 3,702,886; 3,709,979; 3,832,449; 3,998,889, 4,076,842; 4,016,245 and 4,046,859, the disclosures of which are herein incorporated by reference. Further, this invention is applicable to any composition now existing or which may be developed which catalyzes the conversion of alkoxy compounds to hydrocarbon products, especially wherein the catalyst composition exhibits a similar sensitivity to temperature and water concentration in terms of its activity and aging characteristics as now existing MTG catalyst compositions do.

Whatever MTG catalyst composition is selected for use, for essentially complete conversion of the methoxy compound to hydrocarbon to occur, the methoxy containing feed gas must first be conditioned to have about at least a minimum inlet temperature ($T_I$) of about 650° F., and preferably about 700° F. Further, the feed gas should have a specific heat content that limits the temperature increase ($\Delta T_R$) between the inlet temperature ($T_I$) and outlet temperature ($T_R$) of the MTG reactor to less than 100° F., preferably 85° F. or less. The inlet gas temperature may range from about 650° to 720° F. to insure complete conversion, while the outlet temperature should be limited to a range of from about 730°–800° F. To prevent premature aging or damage of the MTG catalyst a temperature of 800° F. should not be exceeded. Also, the partial pressure of steam at the outlet should be limited to a range of 1.85 to 2.2 ata, and preferably 1.95 to 2.15 ata.

Within the broad ranges of inlet and outlet temperature, various narrower ranges are preferred for purposes of product composition and distriBTUion. For example, the amount of durene—an undesirable hydrocarbon component for purposes of fuel uses—has been found to vary with the reaction temperature, increasing with lower reaction temperatures and decreasing with higher temperatures. Accordingly, to minimize durene content while maximizing the fraction of liquid hydrocarbon and the octane value of the liquid hydrocarbon fraction an inlet temperature of at least about 700° F. is preferred. To further insure against premature catalyst aging or destruction a temperature of 785° F. and partial pressure of steam of 2.2 ata at the reactor outlet is preferably not exceeded.

The improved process is based on adiabatic reaction in a multiple reactor system with intermediate injection of colder feed. While the different reactors can easily operate under different conditions, it is easier to explain the new process and its advantages by discussing the special case of all reactor steps operating under similar conditions as to the temperature zone for the contact with the catalyst and the final steam vapor pressure of the reactants in each reactor.

As a typical set of conditions by which to illustrate practice of the process of this invention, unless otherwise indicated, for each reactor in the series a gas stream inlet temperature of 710° F. is used and the gas composition for feed thereto is chosen to provide for a $\Delta T_R$ of 75° F. for an outlet gas of 785° F. at an outlet pressure that provides for a partial pressure of steam of approximately 2 ata. The methoxy feed for each is MeOH, DME, or a mixture thereof as indicated and is as available for use at a temperature of 100° F. The diluent recycle gas is a $C_{2-}$ and $C_{3+}$ gaseous hydrocarbon product of the MTG process or a mixture thereof in a molar ratio that provides a lb-mole quantity thereof to have a specific heat content as indicated. Further, specific heat values of the various components of the involved gas streams are utilized for calculations of the specific heat contents of these gas streams as given in the text which follows. The precise numerical values of these specific heat values may vary somewhat in actual practice with variations in the precise compositions of the components and/or the temperature and pressures to which they are actually subjected, as will be appreciated by those skilled in the art. As desired, in putting this invention into actual practice, one skilled in the art may without undue experimentation determine more precise and accurate numerical values for the circumstances of the actual application. Nevertheless, this would but slightly alter the precise numerical values given hereafter in the discussion of results of the use of this invention, but will not significantly affect the general conclusions discussed about the results and benefits to be had from a practice of this invention.

The Fresh Feed Composition

The composition of fresh feed to be added to a product effluent gas from a preceding MTG reaction to form a combined gas to be fed to a succeeding MTG reaction may be conceptually viewed as comprising two components which in sum equal the fresh feed composition. The first component of the fresh feed is that amount of alkoxy compound that is required to heat up the product effluent gas composition by the delta ($\Delta$) between $T_R$ and $T_I$ ($\Delta T_R$) desired to be achieved in the succeeding MTG reaction. The second component is that quantity of alkoxy plus recycle diluent composition which by itself would react with a $\Delta T_R$ desired for the succeeding MTG reaction (hereafter this component is referred to as the "$\Delta T_R$ balanced alkoxy-recycle diluent composition"). When summed, the first and second components provide for a total fresh feed having a total specific heat content that will cool down the effluent gas by heating up the fresh feed to form a combined gas of the temperature desired as the inlet temperature ($T_I$) for admission to the succeeding MTG reaction. This in turn then dictates the temperature to which the fresh feed must itself be preheated ($T_P$) before being mixed with the product effluent gas which is at its reaction temperature ($T_R$) to form the combined gas at temperature $T_I$ that upon reaction in a succeeding MTG zone will increase in temperature by $\Delta T_R$ to yield a new effluent gas of an out-let temperature as desired, $T_R$.

Wherein one has two gas streams, each being at the same temperature, say $T_R$, then upon mixture of one with the other a combined gas stream of the same temperature $T_R$ is obtained. However, if one takes one gas stream that has already reacted its alkoxy content to reach a temperature of $T_R$ and another gas stream which is at a temperature $T_P$ from which by reaction of its alkoxy content would reach a temperature of $T_R$ and mix the hot with the cooler gas stream a combined gas stream is obtained having a temperature $T_I$ which is less than the $T_R$ of the hot gas stream but greater than $T_P$ of the cooler gas stream. Thereafter the reaction of the alkoxy content of this combined gas stream will elevate its temperature to $T_R$; this because each of the component parts of this combined gas stream—the hot and the cooler gas streams—were either once at the temperature $T_R$ or by reaction of its alkoxy content would be elevated to the temperature $T_R$.

The temperature $T_I$ that is obtained upon mixing of the two gas streams is related to the specific heat content of each, which in turn is related to the composition and quantity of each. Each molecular species comprising either gas stream has a specific heat value in terms of the heat (BTU) required to elevate its temperature (° F.) per a unit quantity (lb-mole) of that species. Herein, specific heat values are given in terms of BTU/° F./lb-mole, meaning the number of BTUs required to elevate one lb-mole of that material by one ° F. The specific heat content of a gas stream is then the number of BTUs required to elevate that gas stream by one ° F., and this specific heat content is the sum of the specific heat value of a species times its quantity for each species contained in the gas stream.

Thus, for example, for methanol ($Q_R$=24,000 BTU/lb-mole) to condition it for reaction to hydrocarbon products such that the temperature increase due to its reaction is 75° F. ($\Delta T_R$) requires that the specific heat content of the feed gas containing this one lb-mole of methanol be 24,000/75=320 BTU/° F. The one lb-mole of methanol itself contributes 16.94 BTU/° F. of this specific heat content, leaving 303.06 BTU/° F. of this content to be satisfied by other components, namely the diluent recycle gas comprising $C_{2-}$, $C_{3+}$, steam, hydrogen or mixtures thereof. For discussion purposes the following specific heat values for such recycle components are assumed; $C_{2-}$ hydrocarbon gas, 13.16 lb BTU/° F./lb-mole:$C_{3+}$ hydrocarbon gas, 36.0 BTU/° F./lb-mole: steam, 8.8 BTU/° F./lb-mole: hydrogen, 8.0 BTU/° F./lb-mole. Selecting a 3:1 molar ratio of $C_{2-}$:$C_{3+}$ hydrocarbon gas as the diluent, this recycle mixture has a specific heat value of [(3×13.16)+(36.0)]/4=18.87 BTU/° F./lb-mole. Then 16.0604 lb-moles of this 3/1 recycle diluent gas would be required for each 1 lb-mole of methanol to form a feed gas that would react with a temperature increase of 75° F. This $\Delta T_R$=75° F. balanced gas composition would then be:

$CH_3OH$=1.00 lb-mole,

Recycle (3/1)=16.064 lb-mole,

Specific Heat Content=320 BTU/° F. This feed as first preheated to 710° F. when contacted with an MTG catalyst will react to form a product gas having a temperature of 785° and a specific heat content which, for discussion purposes, is assumed to be the same as the feed gas from which it was formed, namely 320 BTU/° F.

This hot product gas at 785° F. has a content of heat in excess of that at which it would otherwise have a temperature of 710° F. of 24,000 BTU, which is the heat released by reaction of the methanol from which the product gas stream was formed. Transfer of this 24,000 BTU of heat from this product gas stream to another medium will reduce the temperature of this product gas stream from its 785° F. temperature to a temperature of 710° F. The medium of transfer can be a cooler gas stream, and the transfer can be accomplished by indirect exchange as through the heat transfer surfaces of an adiabatic heat exchanger or by direct gas-to-gas contact by admixture of the two gases.

In this invention the transfer of this excess product heat to the cooler feed gases is in part accomplished through adiabatic heat exchangers—to preheat a fresh feed gas charges to a temperature $T_P$—and in part by direct gas-to-gas contact—to finally warm up the preheated fresh feed gas charges from its $T_P$ preheat temperature to a temperature $T_I$ desired for contacting it with a MTG catalyst. The direct gas-to-gas heat exchange is first accomplished, and the product gas from the last of the MTG reactions in series is used for indirect heat exchange through adiabatic heat exchangers to warm up the fresh feed gases to their preheat $T_P$ temperature.

As to the direct gas-to-gas heat exchange to warm up a fresh feed gas from its preheat temperature $T_P$ to the $T_I$ temperature desired for its contact with an MTG catalyst, the specific heat content of the fresh feed gas governs how much it can be warmed up by the cooling i) down from $T_R$ of the hot product gas with which it is mixed to a temperature $T_I$. The amount by which the fresh feed gas will be warmed up $(T_I—T_P)$, while the product gas is cooled down $(T_R—T_I)$ is related to the ratio of the specific heat content of the fresh feed gas $(S_f)$ to the specific heat content of the product gas $(S_p)$ according to the equation:

$$S_f = \frac{(T_R - T_I)}{(T_I - T_P)} \times (S_P).$$

For the case under discussion, wherein it is desired to have the next reaction begin at a temperature of $T_I$=710° F., the composition and quantity of the new feed gas are governed then by $$S_f(710 - T_P) = 24{,}000,$$

and its specific heat content is a function of the temperature to which it is preheated before admixture with the hot product gas. Selecting then, for discussion purposes, a feed gas preheat temperature of 635° F. $(T_P)$, the specific heat content of the fresh feed must equal that of the product gas with which it is to be mixed, and the combined gas stream will have a specific heat content that is the sum of its component parts. To then have this combined gas stream react to a new product gas temperature $T_R$=785° F. requires that it contain a quantity of alkoxy compound, here for discussion purposes, methanol, to heat its now doubled specific heat content of 640 BTU/° F. by 75° F., or 640×75=48,000 BTU. This quantity of heat is supplied through the reaction of 2 lb-moles of methanol $(Q_R$=24,000 BTU/lb-mole) which contributes 33.88 BTU/° F. towards the needed 320 BTU/° F. specific heat content required for the new feed gas, leaving 286.12 BTU/° F. of the heat content to be supplied by diluent gas. Where this remaining quantity is supplied by a diluent gas comprising a 3/1 molar ratio of $C_2$:$C_{3+}$ hydrocarbon gas, then 15.1627 lb-moles of such recycle gas is required. Hence the composition of the fresh feed gas would be:

CH$_3$OH=2.00 lb-mole,
Recycle (3/1)=15.1627 lb-mole,
Specific Heat Content=320 BTU/° F.

Reaction of the combined gas mixture will then produce a new product gas having a temperature of 785° F. and a specific heat content of 640 BTU/° F.

This new product gas ($T_R$=785° F.; $S_P$=640 BTU/° F.) may be used as the hot gas source for mixture with a new portion of fresh feed gas to form a combined gas mixture for another reaction over an MTG catalyst between any reaction temperature zone of $T_I$ to $T_R$ as may be desired.

Take for instance that for this next reaction it is desired to contact the next MTG catalyst at a temperature $T_I$=700° F. and have a new product gas temperature from that reaction limited to 740° F. In this case the previous product gas requires cool down from 785° F. to 700° F. for a $T_R$-$T_I$ of 85° F., meaning the previous product gas must give up 640 BTU/° F.×85° F.=54,400 BTU of heat which is then available for warm up of the new feed gas to the desired inlet temperature of 700° F. Once this previous product gas component has been cooled to 700° F., at its specific heat content of 640 BTU/° F., to increase its temperature to the $T_R$=740° F. desired for the new product gas requires 640 BTU/° F.×40° F.=25,600 BTU of heat to be released by reaction of methanol contained in the new feed charge. To this end, after reaction by methanol has warmed itself or its reaction product up by 40° F. to consume 16.94×40=677.6 BTU of the heat of its reaction, there remains 24,000−677.6=23,322.4 BTUs of heat to warm up the previous product gas, thus 25,600/23,322.4=1.06667 lb-mole methanol are required to reheat the previous product gas from 700° to 740° F. If again the new feed gas has been preheated to a $T_P$ temperature of 635° F. the composition and quantity of the new feed gas is governed by $$S_F(700 - 635) = 54{,}500$$

or its $S_F$ required is 836.923 BTU/° F. of which 18.594 BTU/° F. is provided by the methanol required to reheat the previous product gas that will become part of the combined gas stream to be reacted. Hence, 818.329 BTU/° F. of value remains to be filled in the new feed gas by methanol and recycle constituents and these constituents must react from a $T_I$ temperature of 700° F. to the new temperature desired of 740° F. Here, to moderate the reaction of one lb-mole methanol to a 40° F. increase in temperature upon its reaction requires a specific heat content of 24,000/40=600 BTU/° F., of which that one-lb-mole of methanol contributes 16.94 BTU/° F., leaving 583.06 BTU/° F. of content to be supplied by a recycle diluent gas. Again, using a 3/1 $C_2$:$C_3$ recycle gas diluent would require 30.8988 lb-mole of such diluent. Hence, the $\Delta T_R$=40° F. balanced gas composition would be:

CH$_3$OH - 1.00 lb-mole,
Recycle (3/1) - 30.8988 lb-mole
Specific Heat=600.0 BTU/° F.

To supply the 818.329 BTU/° F. needed, 1.36388 times this quantity of the $\Delta T_R$=40° F. balanced gas composition is needed. Hence the new feed gas would be:

| | Component To Reheat Previous Product Gas | $\Delta T_R$ = 40° F. Balanced Composition × 1.36388 | New Feed Gas |
| --- | --- | --- | --- |
| CH$_3$OH | 1.097657 | 1.36388 | 2.461538 |
| Recycle | 0 | 42.14231 | 42.14231 |
| Specific Heat Content | 18.594 | 818.329 | 836.923 |

It should be clear from the general discussion given above that in order for the new process to effect significant savings in heat exchange the above mentioned $T_P$ temperature of the added feed should be significantly lower than the $T_I$ temperature of inlet to the reactor obtained after addition of the hot exit gas from the earlier reactor. The given examples clearly demonstrate that a reduction of about a factor of 2 can be obtained with as little as 60° F. difference between these two temperatures. It is, however, preferred to use a more optimal temperature difference of about 200° F. and a larger number of reactors, like 10, preferably 5 to 8, so that a more sizeable heat exchange duty reduction of about one order of magnitude can be obtained, especially when using DME only.

It should be understood that especially when using a larger number of reactors, the resulting pressure drop may begin to exert a negative effect on the size of the heat exchanger. This has been taken into account in calculation of the advantages to be obtained.

Accordingly, to maximize the efficiency of heat exchange operations (which is a variable of pressure and the volume of gas treated for heat exchange) while also maximizing the saving required for fresh feed preheating and/or product gas cooldown for product recovery the following conditions are preferred:

(1) preheating of the fresh feed gas to a temperature within 75° to 260° F. of the $T_I$ temperature selected for admission of the combined gas stream to the succeeding MTG reaction zone, preferably to within 100° to 210° F., and more preferably to within 100° to 160° F.;

(2) formation of the combined gas stream to have a temperature $T_I$ from 650°–720° F., and preferably from about 675°–720° F.;

(3) selection of the alkoxy content of the fresh feed stream to have a heat of reaction content that, upon reaction of that alkoxy content thereof, would increase the temperature of the combined gas stream by a $\Delta T_R$ of 10°–150° F., preferably by 30°–120° F., more preferably by 50°–100° F. and most preferably by 50°–85° F.; and (4) formation from reaction of the combined gas stream in the succeeding MTG reaction zone of a new effluent gas having a temperature $T_R$ of from about 700° to 800° F., preferably from about 730° to 800° F., and more preferably of from about 750 to 785° F.

Reactor Sequence

FIG. 1 illustrates one embodiment of the process which employs five MTG reactors in series flow, reactors 10, 20, 30, 40 and 50. A methoxy feed with an appropriate amount of water to allow initiation of reaction over the MTG catalyst together with an appropriate amount of recycle diluent gas at 100° F., is fed by line 2 to heat exchange 3 and is there preheated to 710° F. then fed by line 4 to the inlet of reactor 10 and passed into contact with an MTG catalyst. The product effluent gas is passed by line 11 to line 12. A fresh quantity of methoxy feed at 100° F. passes from line 5 through heat exchanger 6 and is preheated to a temperature $T_P$ and then passed by line 7 through metering valve 7a into admixture with the product effluent gas in line 12. A further quantity of recycle diluent gas 5a at 100° F. passes through heat exchanger 8 and is preheated to temperature $T_P$ then passed by line 9 through metering valve 9a into admixture with the product effluent gas and methoxy feed in line 12. The combined gas stream passes from line 12 into contact with the MTG catalyst in reactor 20 and the product effluent gases pass therefrom by line 13 into line 14 where the product effluent gas becomes admixed with a further quantity of methoxy feed and recycle diluent gas, each at temperature $T_P$, as metered into line 14 through valves 7b and 9b respectively. Again, the product effluent gas from reactor 30 passes by line 15 into a further quantity of methoxy and recycle gases each at $T_P$ as metered in through valves 7c and 9c respectfully, and the combined gases pass by line 16 into contact with an MTG catalyst in reactor 40. The product effluent gas from reactor 40 passes by line 17 into mixture with a further quantity of methoxy and recycle diluent gas at $T_P$ as metered in through valves 7d and 9d respectively and the combined gases pass by line 18 into contact with an MTG catalyst in reactor 50. The product effluent gas from reactor 50 passes by line 19 to subsequent processing units where it is cooled to 100° F. for separation and recovery of its various components, such as its $C_{2-}$ and $C_{3+}$ hydrocarbon content for recycle use as a diluent gas, its liquid hydrocarbon content to be processed into its fuel grade fractions, and its water content.

Heat Exchange Requirements

In the process of converting an alkoxy compound to hydrocarbon products by contact with an MTG catalyst it is necessary to heat up feedstocks of alkoxy-diluent gases from their unit available temperature $(T_O)$ to a temperature at which they will react over an MTG catalyst, namely $T_I$. By reason of the exothermic reaction of the alkoxy compound to hydrocarbon product the product effluent gas resulting from contact with an MTG catalyst has an even higher temperature, $T_R$. To recover the hydrocarbon product from the reaction gases, it is necessary to cool the product effluent gas from its temperature $T_R$ to a temperature at which its normally liquid hydrocarbon content condenses, typically about 100° F.

Typically, the product gases at $T_R$ and feedstock gases at $T_O$ are passed through adiabatic heat exchangers wherein heat content Q is exchanged between the product gases and feedstock gases through a heat exchange surface that separates these gas streams, whereby the product gases cool down in temperature to the extent they transfer a content Q of their heat to the feedstock gases which are thereby increased in temperature.

In an ideal case, the product gas contains a quantity of heat Q that is in excess of that quantity required to heat up the feedstock gases to $T_P$ by an amount that is equal to the heat released by the alkoxy compound that reacted to form the product gases. Thus, following the first heat exchange between the product gases at $T_R$ and feedstock gases at $T_O$ through the heat exchange surface of an adiabatic heat exchanger, the feedstock gases are heated up to $T_P$ and the reaction gases are cooled down to a temperature $T_x = T_R - (T_P - T_O)$. Hence, to recover normally liquid hydrocarbon compounds from the reaction gases it is necessary to cool them further from their $T_x$ temperature to about 100° F., which is typically the temperature $T_O$ at which the feedstock gases are available since a major portion of the feedstock gases are the $C_{2-}$ and/or $C_{3+}$ hydrocarbon by-products recovered from the reaction gases and used as the recycle or diluent component of a feedstock. In this last step of reaction gas cooling, the reaction gases at $T_x$ are heat exchanged in an adiabatic heat exchanger operating with chill water, typically at a chill water temperature of 70° F.

With the process of this invention it is possible to realize significant economies in the heat exchange requirements in terms of the size of the heat exchangers required for feedstock heatup duties and the heat exchangers required for the final step of reaction C gas cooldown for hydrocarbon product recovery.

Figure 2:
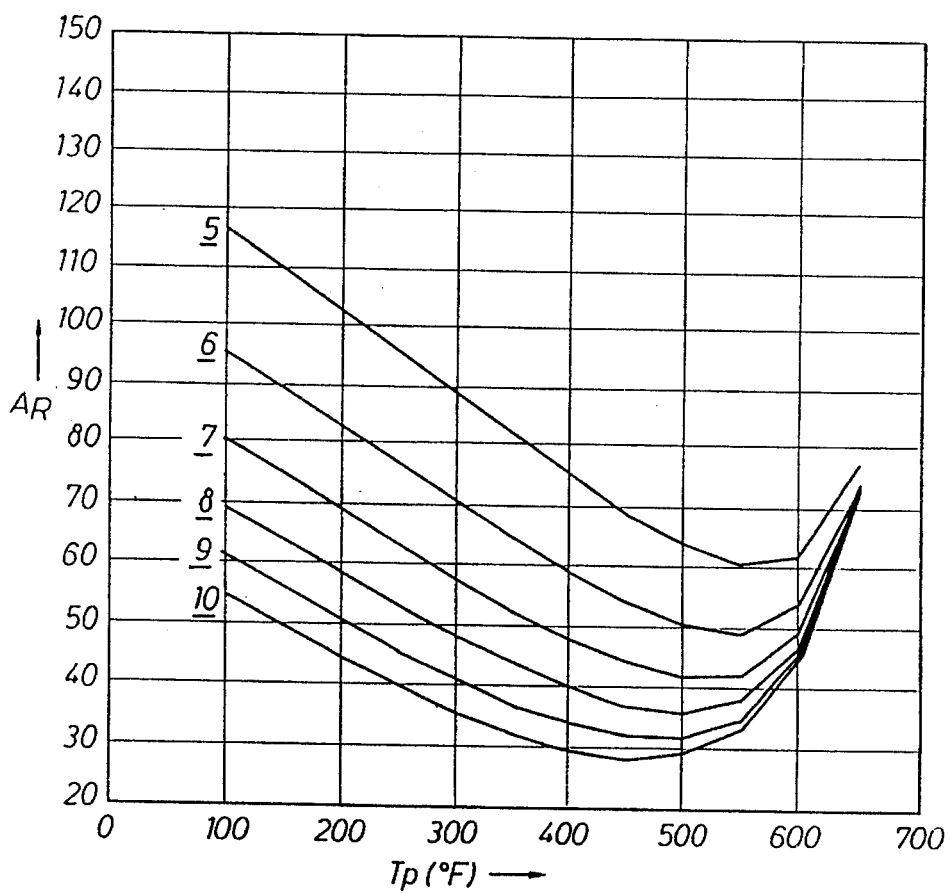
FIGS. 2 and 3 plot the effect on the required relative heat exchanger surface area (Ar) required for performing feed gas warmup by product gas cooldown heat exchange operations in adiabatic heat exchange units in accordance with the process of the invention for different preheat temperatures $T_P$ as employed in a series of from five to ten MTG reactors, wherein a pressure drop of 0.35 ata occurs across each reactor. The relationships illustrated are based upon the general equation $A_R=Q(1/\Delta T)(1/P)^{0.6}$ wherein Q is the quantity of heat involved in a heat exchange operation; $\Delta T$ is the temperature difference between the gases involved in the exchange, namely $T_R-T_P=\Delta T$; and P is the pressure of the gases being heat exchanged. The alkoxy feed for FIG. 2A is dimethyl ether (DME) and for FIG. 3 is a DME containing equilibrium mixture formed from a crude methanol containing 16.4 wt. % water. For comparison treatment of the same quantity of an equilibrium mixture formed from methanol-water in a single reactor requires a relative heat exchange surface area of about 325.4 relative units when operated at a pressure of 22.06 ata to provide for the same partial pressure of steam in the product gas as that provided by the process as illustrated in FIG. 3.
Figure 3:
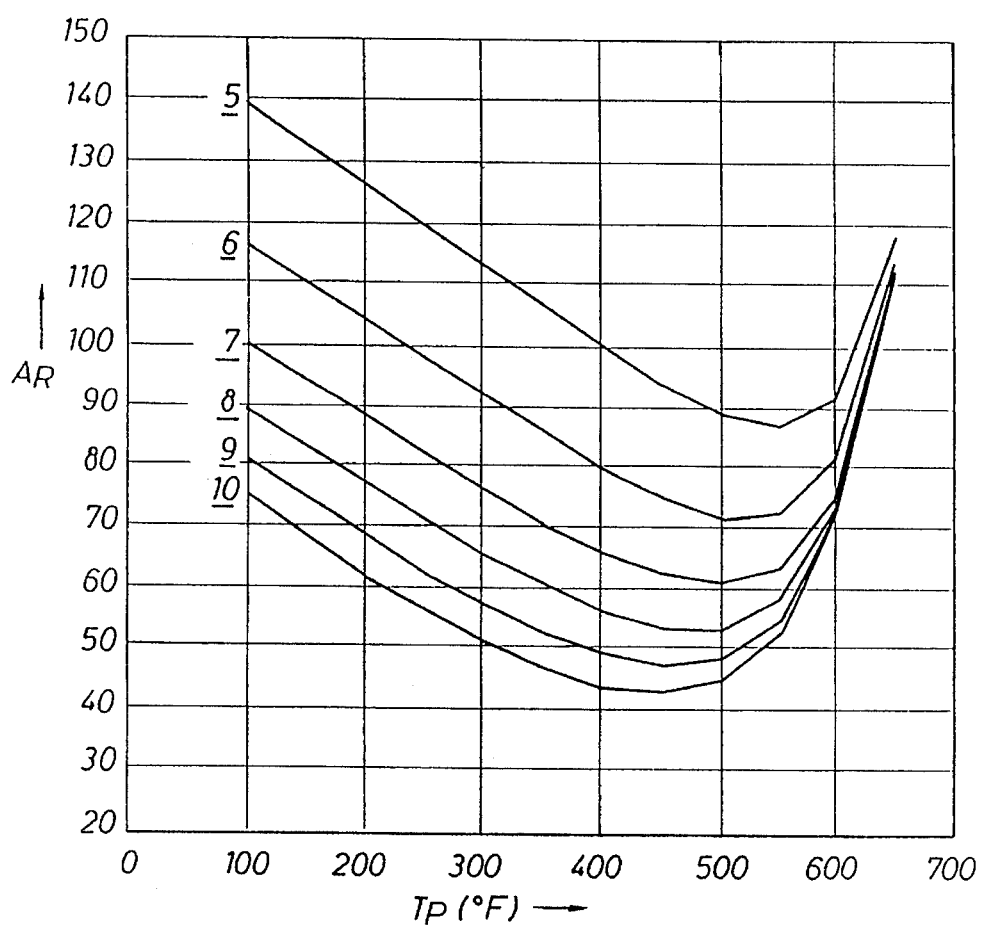

For example, on the basis of methoxy equivalent processed to hydrocarbon product, using as the standard for comparison a process comprising a single reactor pass of the same quantity of methoxy compound for conversion to hydrocarbon product at a reactor inlet temperature of 710° F., and outlet temperature of 785° F. and at an outlet pressure that provides for a partial pressure of water of 2.15 ata and wherein the feedstock gases are available at 100° F. and the recycle diluent gas comprises a 1:3 molar ratio of $C_{3+}:C_{2-}$ hydrocarbon by-product gas, FIGS. 2 and 3 illustrates the affect on the size of the heat exchangers based upon the relative heat exchange surface area ($A_R$) required for feedstock heating.

FIG. 3 is for methanol containing 0.35 moles water per mole of methanol as feed, FIG. 2 is for dry DME as feed.

FIGS. 2 and 3 indicate the results of a series of calculations based on assuming the maximum allowable pressure in the second reactor, reactor II, which is the first reactor with a low amount diluent recycle gas in the feed. From then on a pressure drop per reactor stage of 0.35 ata is taken. The final pressure out of the last reactor is taken as guidance for the size of the relative heat exchanger surface area necessary for warmup of the feeds The heat exchanger for the feed of the first reactor, reactor I, is separately sized from the combined heat exchanger for the combined cold feed. For all reactors in both cases a temperature of reaction is chosen, starting at 710° and ending at 785° F. The added feed is fed in at a series of preheat temperatures $T_P$, varying in steps of 50° F. from 100° to 650° F. The figures clearly show a minimum for the relative heat exchange surface area, that varies with the number of reactor steps used. The minimum seems to be at about the same temperature independent of the nature of the methoxy feed. For both feeds considered, the minimum is at a preheat temperature $T_P$ of about 550° F. for five reactors and slowly decreases to about a rather flat minimum at $T_P$=450° F. with the use of ten stages.

For comparison it should be noted that a one reactor approach as applied to methanol with 0.35 mole of water per mole of methanol requires a heat exchange surface area of about 325.4 relative units on the basis of a pressure of operation of 22.06 ata resulting from the chosen feed. With the same feed the present system with ten stages reduces this heat exchange surface area number to 42.6 relative units while use of DME reduces it further down to 28.5 relative units.

The conclusion is therefore that the process of this invention reduces the required heat exchange surface area for feed gas warm-up between 8 and 10 fold.

As may also be realized, in the process of this invention the use of a recycle diluent gas of a low specific heat content as a feedstock component is preferred to that of a diluent gas of a high specific heat content. As the $C_{2-}$ content of a diluent recycle gas increases at the expense of its $C_{3+}$ content while the specific heat content of the diluent gas remains the same, then the quantity of diluent recycle gas increases and constitutes a larger volume of the final product gas. This in turn means that the water by-product content of the final product gas becomes a small fraction of the total gas content and the gas can be processed at a higher pressure while still maintaining its water content at the same steam partial pressure. For example, where MPH means mole-per-hour, to react 1 MPH methanol ($CH_3OH$) to a hydrocarbon product with a temperature rise of the gas stream limited to 75° F. requires a feed gas composition having a specific heat content of 320 BTU/° F. Of this amount the methanol itself contributes 16.94 BTU/° F. leaving 303.06 BTU/° F. to be supplied by a diluent recycle gas. If supplied solely by a $C_{3+}$ recycle gas then 8.42 MPH $C_{3+}$ recycle would be required and the final product gas would comprise 8.42 $C_{3+}$ recycle, 1 MPH $H_2O$, and 0.1724 MPH hydrocarbon product and a total pressure of 19.18 ata would produce a steam partial pressure of 2.0 ata. On the other hand, if the remainder of the specific heat content required were supplied solely by a $C_{2-}$ recycle then 23.03 MPH $C_{2-}$ recycle would be required and the final product gas would comprise 23.03 MPH $C_2$ recycle, 1 MPH $H_2O$ and 0.1724 MPH hydrocarbon product. At a pressure of 48.40 ata such gas composition would have a steam partial pressure of 2.0 ata. Of the two gas compositions discussed, that using the $C_{2-}$ recycle is more efficiently heat exchanged because of its processing at the higher pressure, in relative terms, requiring only about 57.4% of the heat exchange surface area as would otherwise be required by the gas composition using a $C_{3+}$ recycle. However, the $C_{3+}$ hydrocarbon by-product steam contains olefins and use of a $C_{3+}$ recycle promotes further reaction of the olefin content thereof to $C_{5+}$ hydrocarbons, increasing the yield of the gasoline grade hydrocarbon product. Hence, a reasonable amount of $C_{3+}$ content in the diluent recycle gas is generally desirable. Accordingly, use of the $C_{2-}$ hydrocarbon by-product (specific heat about 13.16 BTU/° F./lb-mole) and diluent gases rich in $C_{2-}$ compared to $C_{3+}$ hydrocarbon by-product, on the order of a $C_{2-}:C_{3+}$ molar ratio of from about 3:1 to about 1:3, as the diluent gas component of a feedstock is preferred.

The preference with respect to the number of reactors in a series and the fresh alkoxy recycle diluent feed preheat temperature are somewhat interrelated. Given the fact that to maintain gas flow through the reaction train a pressure drop must be allowed across each reactor, the number of reactors in a series at which a maximum savings in heat exchange duties per methoxy equivalent converted is limited by this pressure drop factor since lower pressure means lower heat exchange efficiency.

Generally, the maximum in heat exchange economies are realized in the range of fresh feed preheating of about $T_P$=400° to 550° F. Within this range the number of MTG reactors required to realize the maximum in heat exchange required may vary from about 5 to about 10 reactors. In a five reactor series the maximum in heat exchange economy is realized with a preheat of the fresh feeds to about 550° F.; whereas with a fresh feed preheat to 500° F., the maximum in heat exchange economy is realized in the last of a series of six to eight reactors; and at a preheat of 450° F. the maximum economy is realized in the last of a series of nine to ten reactors. On the basis of total methoxy equivalent converted, compared to the relative heat exchange surface area required for feed gas warm-up for conversion in a single reactor pass; in accordance with this invention with a fresh feed gas preheat of 550° F. with a five reactor series requires only about 26.8% of the heat exchange surface area; for a series of six to eight reactions with a fresh feed preheat to 500° F. only 22.1 to 16.3% of the heat exchange surface area is, respectively, required; and for a series of nine to ten reactors with a preheat of 450 only 14.5 to 13.1% of the heat exchange surface area is required.

Product Compositional Control

For purposes of influencing the hydrocarbon distribution of the product in favorable ways, it is possible with the process of this invention to tailor the conditions of inlet-outlet temperature and effluent gas steam partial pressure of water for any reactor in the series to a set of conditions different than other reactors in the series. For example, durene (1,2,4,5 tetramethyl benzene) is not a desirable hydrocarbon component of the product whereas toluene and xylene ("TX" octane boosters) are desirable hydrocarbon components. To minimize the durene and maximize the TX components of the hydrocarbon product, it may be desirable to operate the early reactors in the series at a higher inlet temperature condition (i.e. $T_I \geq 720°$ F.) to decrease aromatic hydrocarbon production therein while operating the last reactor(s) at a lower inlet-outlet temperature condition (i.e., $T_I=700$, $T_R \geq 760°$ F.) to increase aromatic production, but limit or reduce over methylation of the aromatics to durene and/or trimethyl benzene, providing all reactors are operated at a similar partial pressure of water outlet value.

The Recycle Diluent Gas Hydrogen Content

As mentioned before, heat exchangers operate more efficiently at higher rather than lower pressures. As a rule of thumb heat exchange is enhance enhanced by the factor of pressure (P) to the power 0.6. The relative surface area needed therefor is related to pressure by the factor $(I/P)^{0.6}$. Further, with respect to the heat exchange of gases, exchange is more efficient as to species of lower molecular weight than of higher molecular weight. Hence to further enhance the efficiency of heat exchange operations it is preferred to utilize as a diluent gas composition one which incorporates a percentage of hydrogen (specific heat about 8 BTU/° F./lb-mole) ranging from about 10 to about 50 mole % hydrogen and more preferably from about 15 to about 30 mole % hydrogen.

First Reactor Recycle Operation

In another embodiment of the invention the heat exchange duties required for conversion of alkoxyl compound to methanol may be even further reduced by operating the first MTG reactor in a mode wherein a portion of its produce effluent gas is recycled back to its inlet for combination with fresh alkoxy-diluent recycle feedstock admitted thereto.

Figure 4:
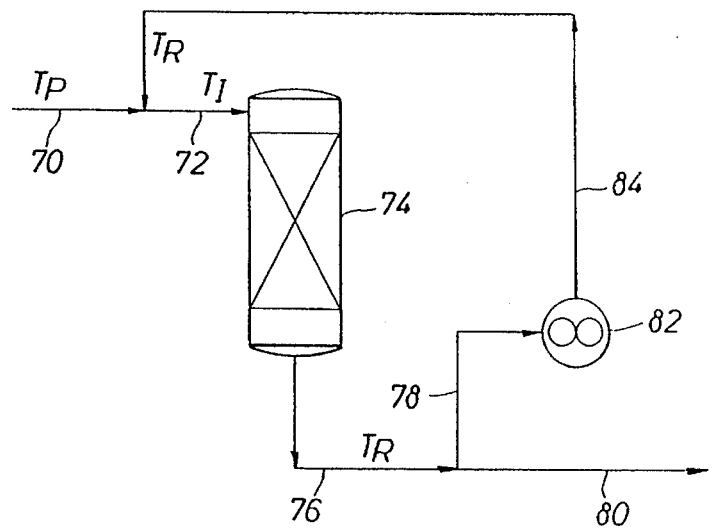
FIG. 4 is a schematic illustration of an alternative embodiment of the process wherein the first of a series of five MTG reactors recycles a portion of its product gas back to the inlet of this first MTG reactor to provide a gas-to-gas exchange of heat with fresh alkoxy feed to this reactor to achieve its final warmup from its $T_P$ temperature to the $T_I$ temperature desired for contact with the MTG catalyst therein.

This mode is illustrated in FIG. 4, wherein feed gas preheated to a temperature $T_P$ is routed by line 70 to the inlet 72 of MTG reactor 74. Product gas at a temperature $T_R$ is taken from reactor 74 by line 76 and is then split into two product streams, one of which proceeds through line 80 to the next MTG reactor in the series (not shown) and the other product gas portion is routed by line 78 to a hot gas fan 82 wherein it is recompressed to a pressure equal to that of the feed gas to MTG reactor 74 and then routed by line 84 for addition to reactor inlet 72 in admixture with feed gas routed to the inlet 72 via line 70. In this mode, as illustrated by FIG. 4, the alkoxy-diluent recycle feedstock would be preheated to a preheat temperature $T_P$ and upon combination with the recycle portion of the product stream at $T_R$ would form a combined gas stream of temperature $T_I$ for contact with the MTG catalyst. In this mode of operation the composition of the alkoxy-diluent recycle feedstock is adjusted to provide an amount of alkoxy compound relative to the diluent recycle content of this feed that upon reaction to hydrocarbon product provides a heat of reaction that raises the temperature of the combined gas stream from $T_I$ to $T_R$. Otherwise stated, the quantity of alkoxy compound relative to the diluent recycle content of the feed is that which by heat of reaction would increase the temperature of the feed alone from its preheat temperature $T_P$ to $T_R$.

This product recycle mode of operation for the first MTG reactor means that preheating of the feedstock gases can more efficiently be accomplished, i.e., a smaller heat exchange area is required, because the differential heat exchange temperature $\Delta T$ as reflected in the heat exchange factor $(1/\Delta T)$ is now $T_R-T_P$ rather than $T_R-T_I$. To accomplish this product recycle requires a slight recompression of this portion of the product gas from its reactor outlet pressure $(P_O)$ to the gas pressure required for the reactor inlet $(P_I)$, in other words, to compensate for the pressure drop occurring across this reactor. This may readily be accomplished with a hot fan, a conventional item of equipment. However to utilize a conventional hot fan for this recompression, the volume of product recycle that can be accomplished is limited by the fan capacity and this in turn will generally set the preference for the conditions to be employed in the subsequent MTG reactors in the series. That is, for a given total of gasoline production desired, once the capacity of the first reactor product recycle is determined, the most optimum of conditions for subsequent feed preheat temperature and the number of MTG reactors may be selected for the balance of the desired gasoline production.

EXAMPLES

The following examples illustrate operations in accordance with the process of the invention and, in some cases, for comparison purposes illustrate operations in accordance with prior art practice. Unless otherwise indicated the following values were applied in preparation of the examples.

Heat of Reaction (1) Dimethylether (DME)→(2/5.8) hydrocarbons+$H_2O$ (35,200 BTT/lb-mole DME)

(2) Methanol (MeOH)→(1/5.8) hydrocarbons+$H_2O$ (24,000 BTU/lb-mole MeOH)

| Specific Heats | BTU/°F./lb-mole |
|---|---|
| (1) DME | 25.08 |
| (2) MeOH | 16.94 |
| (3) $H_2O$ | 8.8 |
| (4) $C_{2-}$ recycle gas | 13.16 |
| (5) $C_{3+}$ recycle gas | 36.0 |
| (6) Hydrocarbon Product | 47.212 |
| (7) $H_2$ | 8.0 |

Operations in accordance with the proposed invention in comparison to that for a single reactor pass method of converting the same quantity of methoxy equivalent is discussed below. In each of Example 1 to 5, unless otherwise indicated, the effluent gas temperature at the outlet $(T_R)$ of each MTG reactor is 785° F., the inlet gas temperature $(T_I)$ of the gas feeds to each MTG reactor is 710F, and the partial pressure of steam in the effluent gas of each MTG reactor is 2.15 ata. A pressure drop of 0.35 ata across each MTG reactor is assumed. Example 1 is a comparative example and illustrates the conversion of the methoxy component of the feed gas by a single pass through one reactor. Examples 2 to 5 illustrate the conversion of a similar quantity of methoxy component in a series of five MTG reactors operating in accordance with the process of this invention. The relative heat exchange surface area $(A_R)$ required for feed gas warm-up in the examples is calculated according to the relationship:

$$A_R = Q\,(1/\Delta T)(1/P)^{0.6}$$

wherein Q is the quantity of heat required to warm-up a feed gas from temperature $T_O$ to $T_P$, with $T_O=100°$ F. for all examples; the $\Delta T$ is $T_R-T_P$ with $T_R=785°$ F. for all examples; and P is the pressure of the last reactor effluent gas and is that pressure in atmospheres absolute (ata) that provides for a partial pressure of steam in the effluent gas of 2.15 ata.

Example 1

Comparative

This example illustrates a single pass conversion of methoxy compound, like that of the single pass process scheme employed in New Zealand. Three situations are presented: (a) wherein the methoxy component is methanol and water in a 1 to 0.35 mole ratio, (b) wherein the methoxy component is an equilibrium mixture made from the methanol-water composition above, and contains methanol, dimethyl ether and water; and (c) wherein the methoxy component is dry dimethyl ether. The recycle diluent gas for each situation comprises a mixture of $C_{2-}$ and $C_{3+}$ hydrocarbon by-product gases wherein the molar ratio of $C_{2-}:C_{3+}$ is 3:1. Quantities are given in lb-moles/hour which is denoted as MPH.

| Feed MPH | (a) MeOH + $H_2O$ | (b) Equilibrium Mix MeOH + DME | (c) Dry DME |
|---|---|---|---|
| MeOH | 28,706 | 7,078 | — |
| DME | — | 10,814 | 14,353 |
| $H_2O$ | 10037.1 | 20,851.1 | — |
| $C_{2-}$ | 342,123.3 | 269,194.0 | 253,255.5 |
| $C_{3+}$ | 114,041.1 | 89,731.3 | 84,451.8 |
| $A_R$ | $10.173 \times 10^6$ | $9.268 \times 10^6$ | $5.031 \times 10^6$ |
| Final P. (ata) | 27.7385 | 22.342 | 53.4792 |

If instead of a recycle gas having a $C_2:C_{3+}$ Mole ratio of 3:1 a recycle gas having a 5:1 ratio were used (which is similar to the actual New Zealand recycle gas) then the relative heat exchange surface area required for the three situations would then be: (a) $9,596\times10^6$; (b) $8,735\times10^6$; and (c) $4.74\times10^6$. It should be noted that with respect to the use of dry DME for a single pass conversion, that the high pressure of greater than 50 ata be viewed as undesirable in that it may promote the production of such a heavy hydrocarbon product as to cause fast cokeing, hence inactivation, of the MTG catalyst. Hence the possible attainment of greater heat exchange economies due to such high pressure operations may be illusory.

Example 2

An equilibrium mixture of 7,078 MPH $CH_3OH$, 10,814 MPH DME and 20,851 MPH $H_2O$ is processed in accordance with the invention in a series of five MTG reactors. For the first MTG reactor of the series a portion of this methoxy content, together with an appropriate amount of $C_{2-}$ and $C_{3+}$ recycle gas of a $C_{2-}:C_{3+}$ ratio of 3:1 and a quantity of water to provide for a reactor outlet steam pressure of 2.15 ata is preheated to 710° F., the remainder of this methoxy content is combined with the $C_{2-}$ and $C_{3+}$ recycle gas of 3:1 mole ratio and preheated to the $T_P$ temperature indicated and proportioned as fresh feed to the four subsequent MTG reactors wherein each portion is combined with the effluent gas from a preceding MTG reactor before being fed to its succeeding MTG reactor. The relative heat exchanger surface areas required for preheating the feed to the first reactor, Reactor I, and for preheating the feeds for the subsequent four reactors, Reactors II–V, are given below, as is the total of the relative heat exchange surface area required.

| $T_P$: Temperature (°F.) Fresh Feed Preheat for Reactors II–V | Final Product Gas Pressure, (ata) | Relative $A_{RI}$: Heat Exchange Surface Area, Reactor I, ($\times 10^6$) | Relative $A_{II-V}$: Heat Exchange Surface Area, Reactors II–V ($\times 10^6$) | Total Heat Exchange Surface Area ($\times 10^6$) |
|---|---|---|---|---|
| 650 | 11.6 | 0.304 | 3.746 | 4.050 |
| 600 | 8.6 | 0.902 | 2.098 | 3.000 |
| 550 | 7.2 | 1.472 | 1.266 | 2.739 |
| 500 | 6.1 | 2.006 | 0.828 | 2.834 |
| 450 | 5.4 | 2.463 | 0.556 | 3.018 |
| 400 | 4.8 | 2.893 | 0.382 | 3.276 |

The above data demonstrates that as the fresh feed gas preheat temperature $T_P$ is lowered, meaning that the relative proportion Of the fresh feed being mixed with the hot effluent gas from a preceding reactor becomes smaller, that the contributon of the heat exchange duty requirements for preheating the first reactor feed gas to the total heat exchange duties becomes greater. As a consequence, even though of the total methoxy converted that converted in the first reactor is a small fraction, the requirements for its warm-up together with its recycle gas content is of major influence on the total heat exchange area necessary. If instead of a recycle gas having a $C_{2-}:C_3$ mole ratio of 3:1 a recycle gas having a mole ratio of 1:3 were used, then, using the $T_P$ condition of 600° F. for comparison, the total relative heat exchange surface area required would be $3,760\times10^6$, this being due to the lower pressure of operation required to maintain the steam partial pressure in the final effluent gas at 2.15 ata.

Example 3

In a manner like that of Example 2, 14,353 MPH dry dimethyl ether is used as the alkoxy component of the feed. The following results are given:

| $T_P$: Temperature (°F.) Fresh Feed Preheat for Reactors II–V | Final Product Gas Pressure, (ata) | $A_R$: Relative Heat Exchange Surface Area, Reactor I, ($\times 10^6$) | $A_{R\,II-V}$: Relative Heat Exchange Surface Area, Reactors II–V ($\times 10^6$) | $A_{R\,TOTALS}$: Total Relative Heat Exchange Surface Area ($\times 10^6$) |
|---|---|---|---|---|
| 650 | 28.6 | 0.162 | 1.995 | 2.156 |
| 600 | 20.6 | 0.489 | 1.139 | 1.628 |
| 550 | 16.6 | 0.818 | 0.704 | 1.522 |
| 500 | 13.6 | 1.137 | 0.469 | 1.606 |
| 450 | 12.1 | 1.391 | 0.314 | 1.705 |
| 400 | 9.6 | 1.869 | 0.149 | 2.018 |

If instead of a recycle gas having a $C_{2-}:C_{3+}$ mole ratio of 3:1 a recycle gas having a mole ratio of 1:3 were used, then, using the $T_P$ condition of 600° F. for comparison, the total relative heat exchange surface area required would be $2.087\times10^6$.

Example 4

The same methoxy feed composition as in Example 2 is utilized under similar conditions except that the first MTG reactor is now operated in a mode wherein a portion of its product gas is recycled back to its inlet and mixed with feed gas thereto. Further, the feed gas to the first MTG reactor is now preheated to either 600° F. or 650° F., as indicated below, and by combining it with the portion of product recycle, a combined gas stream of 710° F. is formed for inlet to the first reactor.

| $T_P$: Reactor Feed Preheat Temp., (°F.) | Final Product Gas Pressure (ata) | $A_{R\ I}$: Relative Heat Exchange Surface Area, Reactor I | $A_{R\ II-V}$: Relative Heat Exchange Surface Area, Reactors II–V | $A_{T\ TOTAL}$: Total Relative Heat Exchange Surface Area |
|---|---|---|---|---|
| I @ 600° F. |  | $0.289 \times 10^6$ |  |  |
| II–V @ 600° F. | 8.04 |  | $2.022 \times 10^6$ | $2.311 \times 10^6$ |
| I @ 650° F. |  | $0.433 \times 10^6$ |  |  |
| II–V @ 600° F. | 8.6 |  | $2.010 \times 10^6$ | $2.442 \times 10^6$ |

Example 5

The same methoxy feed composition as in Example 3 is utilized under similar conditions except that the first MTG reactor is now operated in a mode wherein a portion of its product gas is recycled back to its inlet and mixed with feed gas thereto. Further, the feed gas to the first MTG reactor is now preheated to either 600° F. or 650° F., as indicated below, and by combining it with the portion Of product recycle, a combined gas stream of 710° F. is formed for inlet to the first reactor.

| $T_P$: Reactor Feed Preheat Temp., (°F.) | Final Product Gas Pressure (ata) | $A_{R\ I}$: Relative Heat Exchange Surface Area, Reactor I | $A_{R\ II-V}$: Relative Heat Exchange Surface Area, Reactors II–V | $A_{R\ TOTALS}$: Total Relative Heat Exchange Surface Area |
|---|---|---|---|---|
| I @ 600° F. |  | $1.60 \times 10^6$ |  |  |
| II–V @ 600° F. | 18.6 |  | $1.121 \times 10^6$ | $1.281 \times 10^6$ |
| I @ 650° F. |  | $0.250 \times 10^6$ |  |  |
| II–V @ 600° F. | 18.6 |  | $1.160 \times 10^6$ | $1.409 \times 10^6$ |

By comparison of the data presented in Example 1–5, it is apparent that the process of this invention results in a significant reduction in the heat exchange duties required for feed gas warm-up. Hence, using the equilibrium methanol-DME-$H_2O$ as the methoxy component of the feed of situation (b) of Example 1 for comparison, even at a lesser than most optimum feed gas preheat of $T_P$=600° F. (the optimum being 550° F.), as illustrated by Example 2 the same equilibrium methanol-DME-$H_2O$ component may be converted with only 32% of the heat exchange requirement of Example 1. As illustrated by Example 3, use of a dry DME as the methoxy component of the feed gas in an amount equal in methoxy equivalent to the equilibrium methanol-DME component of Example 1 allows for conversion with only 17.67% of the heat exchange requirement of Example 1. Further as illustrated in Example 3, at the feed gas preheat temperature of 600° F. the operational pressure with respect to the dry DME used is 20.6 ata, hence no concern about possible coke over of the MTG catalyst should arise. Further, as illustrated in Example 5, the heat exchange requirements for processing dry DME according to the invention may be further reduced to only about 13% of that required in Example 1 by operating the first MTG reactor in a mode wherein a portion of its effluent gas is recycled back to its inlet to assist in feed gas warm-up.

Also to be realized in the practice of this invention is a reduction in the heat exchange duties required for the final step of product gas cool-down to recover its liquid hydrocarbon content. Hence, with respect to the product gas resulting in Example 1 from the conversion of the equilibrium mixture of DME—$CH_3OH$—$_{H2}O$, the final product gas after heat exchange through an adiabatic heat exchanger to warm feed gas up has a first cooldown temperature around 175° F. By contrast the final product gas resulting from the preheat $T_P$=600° F. process of Example 2 after heat exchange through adiabatic heat exchangers to warm-up feed gas has a first cooldown temperature $T_X$ around 285° F.

With the process of this invention the final cooldown of the product gas for liquid hydrocarbon recovery requires a smaller heat exchanger because the heat exchanger needed to cool this gas operates with a larger differential temperature, $\Delta T$, for the needed cool down.

Although the process of this invention has been described with reference to its preferred embodiment, from this description those skilled in the art may appreciate changes and modifications that may be made which do not depart from the scope and spirit of the invention as described above and claimed hereafter.

I claim:

1. A method of making hydrocarbon compounds by contacting an alkoxy compound with an MTG catalyst, comprising the steps of:

combining an effluent gas product from a preceding MTG reaction zone which is at a temperature $T_R$ with
 (a) an alkoxy compound; and
 (b) a diluent gas comprising a $C_{2-}$ recycle gas, a $C_{3+}$ recycle gas, steam, hydrogen, or mixtures thereof, to form a combined gas stream wherein in the combined gas stream;
 1. the alkoxy compound is present in a quantity that provides an alkoxy equivalent which exceeds that added to the preceding MTG reaction zone from which the effluent product gas was formed; and
 2. the diluent gas composition is of a temperature and composition and is present in an amount that:
   (a) provides for the combined gas stream to have a temperature of from about 650° F. to about 720° F., and
   (b) provides for the combined gas stream to have specific heat content that limits temperature increase of the gas stream to less than 150° F. upon reaction of the alkoxy compound content thereof to hydrocarbon compounds;
   (c) provides for a total water content following reaction of the alkoxy compound to hydrocarbon compounds that does not exceed a partial pressure of water (as steam) of 2.2 ata; and contacting the combined gas stream with an MTG catalyst in a succeeding reaction zone to form a new effluent product gas.

2. The method of claim 1, wherein the combined gas stream has a temperature of from about 700° to about 720° F., and the temperature increase of the gas stream is less than 100° F.

3. The method of claim 2, wherein the alkoxy compound is DME and the diluent gas comprises a $C_{2-}$ recycle gas and a $C_{3+}$ recycle gas in a molar ratio of $C_{2-}:C_{3+}$ of from about 3:1 to about 1:3.

4. The method of claim 3, wherein the diluent gas contains from about 10 to about 50 mole % of hydrogen.

5. The method of claim 1, wherein from three to ten MTG reaction zones are arranged in series flow, and the combined gas stream comprising the effluent gas product from a preceding MTG reaction zone and the alkoxy compound and diluent gas is at a temperature of from about 675° to about 720° F. when first contacted with an MTG catalyst in a succeeding MTG reaction zone and has a specific heat content that provides for a temperature of effluent gas exiting the succeeding zone of from about 730° to about 800° F.

6. The method of claim 5, wherein with respect to each MTG reaction zone each combined gas stream enters each zone at substantially the same inlet temperature and each effluent gas exits each zone at substantially the same outlet temperature.

7. The process of claim 6, wherein the partial pressure of water in an effluent gas does not exceed 2.2 ata.

8. The method of claim 1, wherein the alkoxy compound and diluent gas are preheated to a temperature of from about 450° to about 550° F. prior to being combined with the effluent gas product from a preceding MTG reaction zone.

9. The method of claim 8, wherein the combined gas stream has a temperature of from about 650° to 720° F. and the temperature increase of the gas stream is about 85° F. or less.

10. The method of claim 9, wherein the alkoxy compound is DME and the diluent gas comprises a $C_{2-}$ recycle gas and a $C_{3+}$ recycle gas in a molar ratio of $C_{2-}:C_{3+}$ of from about 3:1 to about 1:3.

11. The method of claim 1, wherein a series of MTG reactors is employed and the combined gas stream supplied to the last MTG reactor of the series has a temperature of from about 650° to 700° F. and a specific heat content that limits the new effluent product gas temperature to 760° F. or less.

12. The method of claim 11, wherein the combined gas stream supplied to the MTG reactors other than the last MTG reactor of the series has a temperature of 710° to 730° F. and a specific heat content that limits its temperature increase to a range of 70° to 90° F.

13. The method of claim 1, wherein a series of MTG reactors is employed and a portion of the effluent product gas from the first MTG reactor is recycled back to the first MTG reactor inlet to become admixed with feedgas to the first MTG reactor to form a combined gas stream feed to the first MTG reactor having a temperature of from about 650° to 720° F. and a specific heat content that limits temperature increase of the gas stream to less than 150° F.

14. The method of claim 13, wherein the combined gas stream feed to the first MTG reactor has a temperature of from about 650° to about 720° F. and a specific heat content that limits temperature increase of the gas stream to 100° F. or less.

15. The method of claim 1, wherein the diluent gas contains steam in an amount sufficient to provide for a partial pressure of steam in the new effluent product gas of from about 1.95 to about 2.2 ata.

16. The method of claim 1, wherein a series of MTG reactors is employed, and of that total quantity of alkoxy compound converted to hydrocarbon compounds, no more than 20% of the total alkoxy compound is converted in the first MTG reactor of the series.

17. The method of claim 1, wherein each effluent gas product has a partial pressure of water of from 1.85 to 2.2 ata.

* * * * *